United States Patent [19]

Hinchliffe

[11] Patent Number: 5,591,180
[45] Date of Patent: Jan. 7, 1997

[54] SURGICAL SUTURING APPARATUS

[75] Inventor: Peter W. J. Hinchliffe, New Haven, Conn.

[73] Assignee: United States Surgical Corporation, Norwalk, Conn.

[21] Appl. No.: 425,130

[22] Filed: Apr. 19, 1995

[51] Int. Cl.⁶ .................................................. A61B 17/00
[52] U.S. Cl. ........................ 606/144; 606/139; 606/148; 112/169
[58] Field of Search .................................. 606/139, 144, 606/145, 147, 148, 151, 205–208; 112/169, 80.03, 80.06; 604/158, 161, 163, 164, 171

[56] References Cited

U.S. PATENT DOCUMENTS

| 86,016 | 1/1869 | Howell | 606/206 |
|---|---|---|---|
| 659,422 | 10/1900 | Shidler . | |
| 1,037,864 | 9/1912 | Carlson et al. . | |
| 1,822,330 | 9/1931 | Ainslie . | |
| 2,601,564 | 6/1952 | Smith . | |
| 2,880,728 | 4/1959 | Rights . | |
| 3,168,097 | 2/1965 | Dormia . | |
| 3,470,875 | 10/1969 | Johnson . | |
| 3,807,407 | 4/1974 | Schweizer . | |
| 3,842,840 | 10/1974 | Schweizer . | |
| 3,901,244 | 8/1975 | Schweizer . | |
| 4,164,225 | 8/1979 | Johnson et al. . | |
| 4,493,323 | 1/1985 | Albright et al. . | |
| 4,545,374 | 10/1985 | Jacobson | 606/17 |
| 4,827,931 | 5/1989 | Longmore . | |
| 4,841,888 | 6/1989 | Mills et al. . | |
| 4,890,615 | 1/1990 | Caspari et al. . | |
| 4,923,461 | 5/1990 | Caspari et al. . | |
| 4,935,027 | 6/1990 | Yoon . | |
| 4,957,498 | 9/1990 | Caspari et al. . | |
| 5,047,039 | 9/1991 | Avant et al. . | |
| 5,080,663 | 1/1992 | Mills et al. . | |
| 5,188,636 | 2/1993 | Fedotov | 606/144 |
| 5,364,408 | 11/1994 | Gordon . | |
| 5,368,601 | 11/1994 | Sauer et al. . | |
| 5,403,328 | 4/1995 | Shallman . | |
| 5,431,666 | 7/1995 | Sauer et al. | 606/139 |

FOREIGN PATENT DOCUMENTS

| 0140557 | 5/1985 | European Pat. Off. . | |
|---|---|---|---|
| 4137218 | 2/1993 | Germany . | |
| 1093329 | 5/1984 | U.S.S.R. . | |
| WO9106247 | 5/1991 | WIPO . | |
| WO9301750 | 4/1993 | WIPO . | |
| WO/94/17737 | 8/1994 | WIPO | 606/144 |

OTHER PUBLICATIONS

REMA Brochure, Germany (1992).

Primary Examiner—Michael Powell Buiz
Assistant Examiner—Jeffrey A. Schmidt

[57] ABSTRACT

An apparatus for suturing body tissue is disclosed comprising first and second elongated body halves detachably connected to one another and first and second needles movable with respect to the first and second body halves. Each of the needles has a penetrating tip facing in a distal direction. At least one actuator is provided which is operatively associated with each of the first and second needles, wherein actuation of the at least one actuator advances the first and second needles into body tissue. The needles are advanced through the body tissue positioned in the window formed in each of the body halves to engage a ferrule having a suture connected thereto.

20 Claims, 6 Drawing Sheets

FIG_11

SURGICAL SUTURING APPARATUS

BACKGROUND

1. Technical Field

This application relates to a surgical apparatus for suturing body tissue, and more particularly to an endoscopic apparatus for closing an incision created by a trocar.

2. Background of Related Art

Endoscopic and laparoscopic surgical procedures are performed through access ports or through small incisions in the body tissue. When performed through access ports, a plurality of trocars comprising an obturator with a sharp penetrating tip and a hollow cannula are inserted through the skin and underlying tissue layers into the body cavity. The obturator is then removed, leaving the cannula positioned in the body to provide an access port to the surgical site for introduction of a variety of surgical instruments such as staplers, clip appliers, scissors, retractors and graspers to perform the surgical procedure. At the end of the surgical procedure, the cannulas are withdrawn from the body tissue leaving an opening usually ranging from 5 to 20 millimeters, depending on the size of the cannula being used.

Typically, these trocar incisions are closed by the surgeon manually suturing the wound edges. However, such suturing does not always effectively close the lowermost layers of tissue, e.g., the muscle and fascia layers, thereby providing sub-standard wound closure.

Inadequate tissue re-approximation and subsequent poor healing of trocar sites can lead to wound closure defects in the abdominal wall. Abdominal contents, often bowel or mesentery, can bulge, (i.e. herniate) through such a defect.

Several attempts have been made to design instruments to effectively and expeditiously close trocar incisions. One such instrument is disclosed in U.S. Pat. No. 5,368,601 to Sauer. This instrument contains two needles which are deployed inside the body cavity with the pointed tips facing upwardly towards the skin. U.S. Pat. No. 5,320,632 to Heidmueller discloses a wound closure instrument having a pair of needles pointed upwardly and a slidable needle shield to capture the needle tips when pulled upwardly through the skin. Another type of wound closure device is disclosed in U.S. Pat. No. 5,364,482 to Gordon. In Gordon, a pair of curved needles are deployed from the apparatus in an arcuate path to penetrate the lowermost layers of the wound.

The need exists for an improved apparatus to close trocar incisions. It would be advantageous if the device effectively closed the lower muscle and fascia layers of the wound. It would also be advantageous if the device could effectively control and ensure proper placement of the suture in the desired position.

SUMMARY

An apparatus for suturing body tissue is disclosed comprising first and second elongated body halves detachably connected to one another, and first and second needles movable with respect to the first and second body halves. Each of the needles has a penetrating tip facing in a distal direction. At least one actuator is provided which is operatively associated with the first and second needles for advancing the first and second needles into body tissue. The at least one actuator preferably comprises first and second tabs slidably mounted with respect to the first and second body halves to drive the first and second needles distally into body tissue.

Each of the body halves preferably has a window formed therein for receiving body tissue. A first ferrule is positioned in the distal end portion of the first body half and a second ferrule is positioned in the distal end portion of the second body half. A suture is connected at one end to the first ferrule and at the other end to the second ferrule. Actuation of the first and second tabs advances the first and second needles through the body tissue into engagement with the first and second ferrules to effectively pick up the suture.

The elongated body halves, when attached, have a central bore formed therethrough dimensioned for receiving a trocar cannula. The body halves are removably mountable to the outer surface of the trocar cannula and are preferably detachably connected to one another at a proximal end portion.

A method for closing trocar wounds is also disclosed comprising inserting a trocar cannula into a bore in a suturing apparatus having first and second body halves and first and second needles, inserting the apparatus into the body cavity through the trocar wound, advancing the first needle through the first body half and the second needle through the second body half to penetrate body tissue, retracting the first and second needles within the first and second body halves, and separating the first and second body halves from each other. The step of advancing the first and second needles includes the step of advancing the needles in a distal direction and connecting each needle to a portion of the suture attached to first and second ferrules positioned in a distal end portion of the body halves.

The method may also include the steps of withdrawing the first and second body halves from the body cavity to pull the suture through the body tissue, removing the suture from the ferrules, and wrapping the suture around a cannula fastening device.

BRIEF DESCRIPTION OF THE DRAWINGS

Various embodiments of the surgical apparatus of the subject application will be described below with reference to the following drawings wherein.

DETAILED DESCRIPTION OF THE PREFERRED EMBODIMENTS

Figure 1:
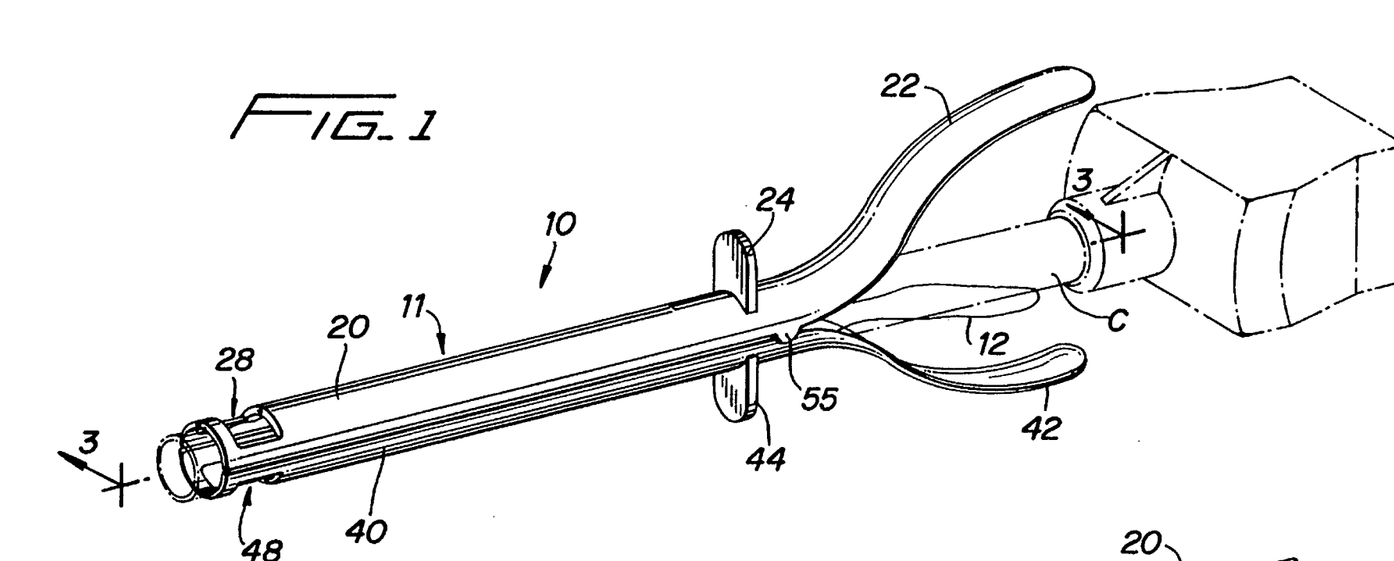
FIG. 1 is a perspective view of the surgical apparatus for suturing body tissue shown mounted over a trocar cannula.

Referring now to the drawings and in particular to FIG. 1, a surgical apparatus, designated generally by reference numeral 10, is provided for closing incisions in body tissue. During endoscopic or laparoscopic procedures, several trocars are inserted through the skin and underlying tissue layers into the body cavity. The trocar typically includes an obturator having a piercing tip and a hollow cannula. After insertion, the obturator is removed, leaving the cannula in place to provide an access port for endoscopic instruments such as staplers, clip appliers, graspers, scissors and other instruments necessary to perform the surgical procedure. At the end of the surgical procedure, an incision remains through the underlying tissue layers, created by the trocar, which the apparatus 10 disclosed herein is designed to close.

Figure 2:
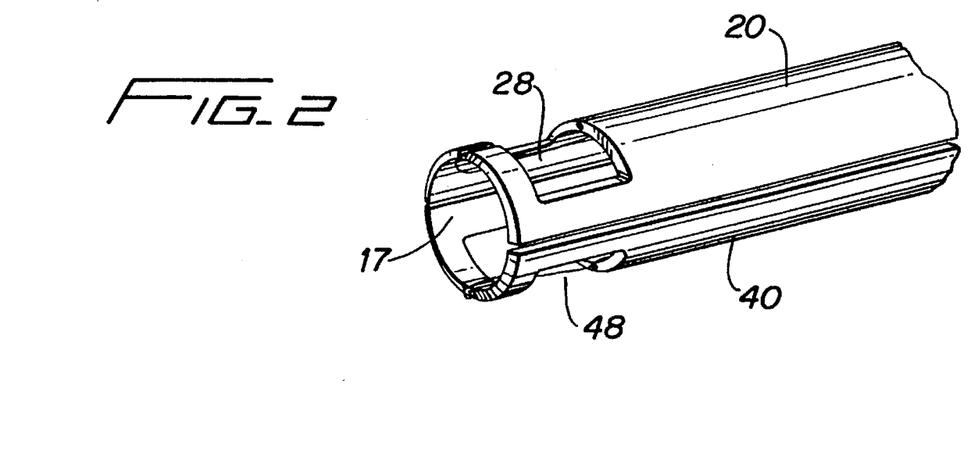
FIG. 2 is an enlarged perspective view of the distal end portion of the apparatus of FIG. 1.

Referring first to FIGS. 1 and 2, the apparatus 10 has an elongated body portion or shaft 11 comprising elongated body halves 20 and 40 which are detachably connected to each other. Elongated body portion has an axial bore 17 extending the length thereof. The trocar cannula C is positioned within the axial bore 17 and the apparatus 10 and cannula are inserted into the body cavity. Once the apparatus is properly placed adjacent to the tissue to be sutured, the two body halves are pivoted outwardly to capture tissue in the windows 28, 48. A needle driving mechanism or actuator in the form of driver tabs 24, 44 is pressed distally to advance a pair of surgical needles through the body tissue positioned in the windows 2848. The needles each engage a ferrule, having a suture attached thereto, positioned in the distal end portion of the apparatus. In this manner, when the needles are retracted to their initial position, they carry their associated ferrules and connected suture through the body tissue to place the suture on both sides of the trocar incision. The suture is then separated from the apparatus, tensioned, and manually tied from outside the body to approximate the tissue on both sides of the trocar incision and to close the incision.

Turning now to the individual components of the surgical suturing apparatus 10, and with continued reference to FIGS. 1 and 2, the elongated body portion 11 preferably has an inner diameter slightly larger than the outer diameter of a trocar cannula which typically ranges between 5 and 20 millimeters. As noted above, body portion 12 is formed by elongated housing halves 20 and 40 which are connected at pivot point 55. Pivot point 55 is also the location where the two body halves 20, 40 are detachably fitted together which is discussed in more detail below. The distal end of the body halves 20, 40 can optionally be chamfered to facilitate ease of insertion into the incision.

Figure 3:
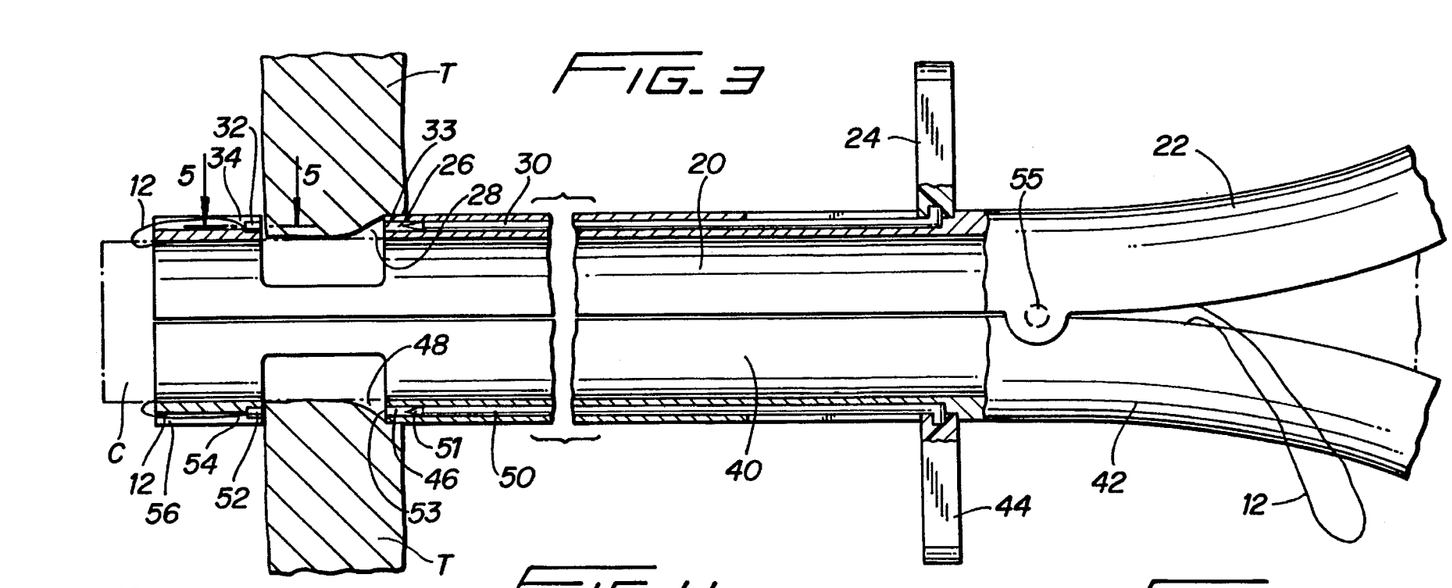
FIG. 3 is a cross-sectional view taken along lines 3—3 of FIG. 1 showing the apparatus positioned in the body cavity and the needles in the retracted position.
Figure 4:
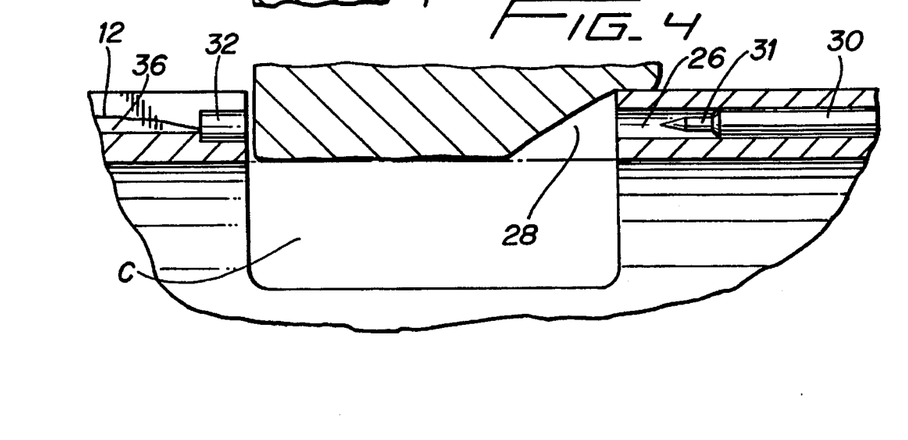
FIG. 4 is an enlarged cross-sectional view of the distal end portion of the apparatus showing one of the needles in the retracted position.
Figure 5:
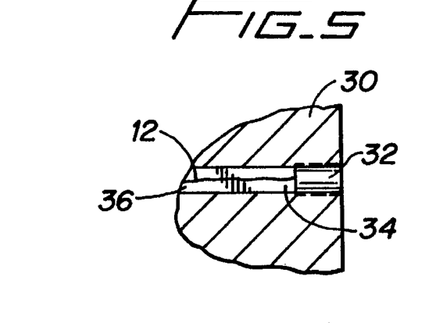
FIG. 5 is an enlarged cross-sectional view taken along lines 5—5 of FIG. 3 showing one of the ferrules positioned in a recess in the elongated body half.

Body half 20 has a handle 22 at its proximal end, extending away from the longitudinal axis of the body portion 12, to facilitate manipulation by the user. An elongated slot 26, best shown in FIG. 3, is dimensioned to receive a needle 30. Driver tab 24 extends perpendicularly from body half 20 and is mounted to the proximal end of needle 30. Sliding movement of driver tab 24 distally drives the needle 30 distally.

A needle engaging member or ferrule 32 is positioned in a recess 34 at the distal end portion of body half 20. A suture 12 is connected at one end to ferrule 32 and extends through body half 20. When the needle 30 is advanced, its distally facing penetrating tip 31 is advanced into frictional engagement with the ferrule 32 to pick up the suture in the manner described below.

Body half 40 is similar in configuration to body half 20. Needle 50, with distally facing penetrating tip 51, is slidably seated within elongated slot 46. Driver tab 44, positioned distally of handle 42, is connected to needle 50 for advancing needle 50 into engagement with ferrule 52 positioned in a recess 54 in the distal end portion of body half 40. Ferrule 52 is connected to the opposite end of suture 12. Ferrule 52, is identical to ferrule 32, both of which are preferably substantially cylindrical in configuration and have a bore for receiving the penetrating tip of the needle.

Elongated body halves 20 and 40 are snap fitted together at pivot point 55. Thus, the user can grasp handles 22 and 42 and squeeze them together to cause the distal end portions of body halves 20 and 40 to pivot away from each other. The two body halves can also be detached at pivot point 55 to separate the body halves in the manner described below. In a preferred embodiment, one body half has a protrusion and the other body half has an indentation dimensioned to receive the protrusion.

Figure 8:
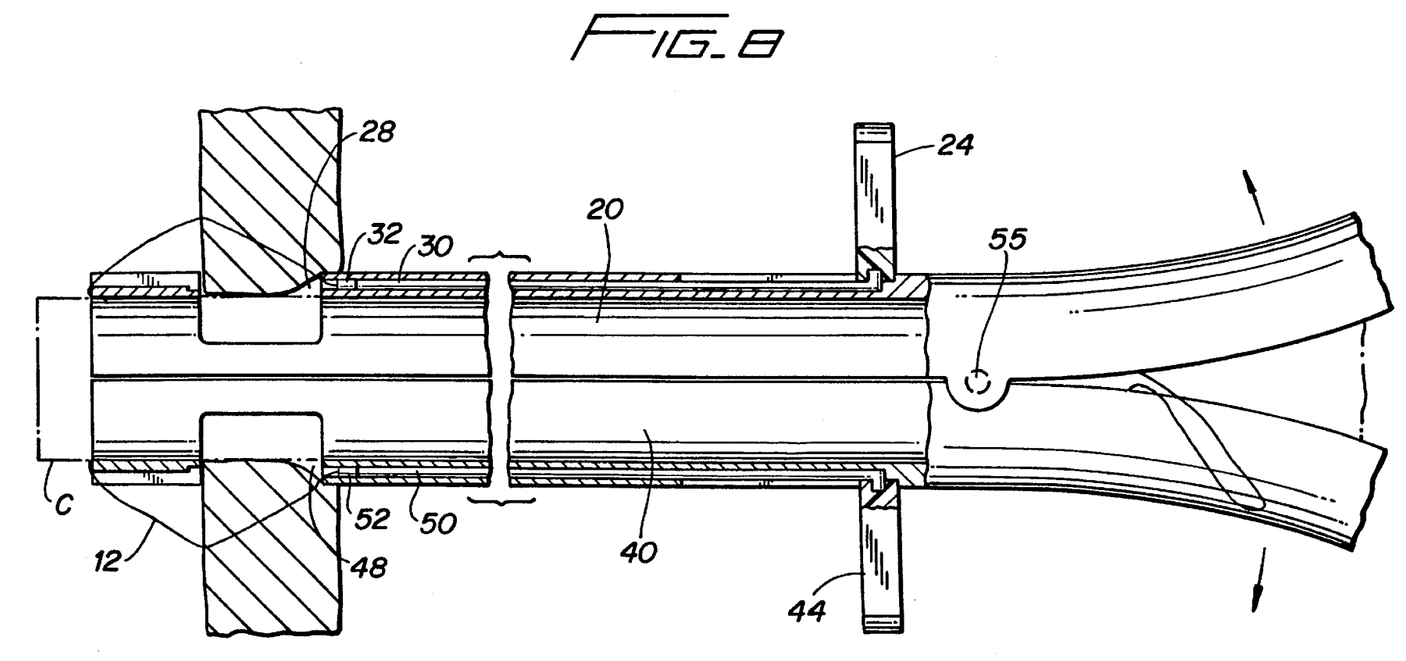
FIG. 8 is a cross-sectional view similar to FIG. 3 showing the elongated body halves returned to their initial position and the needles in the retracted position after engagement with their respective ferrules.

Suture 12 is attached at one end to ferrule 32, extends through a guide slot 36 formed in body half 20, into guide slot 56 of body half 40, and is attached at its other end to ferrule 52. When the needle driving tabs 24, 26 are slid distally, needles 30, 50 are forced out of their respective exit openings 33, 53, through the body tissue seated in windows (recesses) 28, 48, and into frictional engagement with ferrules 32, 52 positioned in the recesses 34, 54 of body halves 20, 40. As a result, the surgical needles 30, 50 effectively become connected to the suture 12. (see FIG. 7) Thus, when the needles 30, 50 are retracted back through exit openings 33, 53 and into elongated slots 26, 46, the frictional engagement of the needle tips 31, 51 with the ferrules 32, 52 pulls the ferrules and attached suture 12 proximally through the tissue and into the elongated slots as shown in FIG. 8.

The use of the surgical suturing apparatus 10 for closing an incision created by a trocar during an endoscopic/laparoscopic procedure will now be described. As noted above, during endoscopic procedures, where surgery is performed inside the body cavity, one or more trocars are inserted through the body tissue to access the body cavity. A typical trocar includes an obturator having a sharp penetrating tip removably mounted within a cannula. After insertion of the trocar into the body cavity, the obturator is removed leaving the cannula in place to provide an access port for the insertion of various surgical instruments for performing the endoscopic/laparoscopic surgical procedure. The apparatus 10 disclosed herein is positioned over the trocar cannula C as shown in FIG. 1. Note that the apparatus can come prepackaged positioned over the cannula C or alternatively packaged unattached where the user simply inserts the cannula C through the axial bore 17 formed in the body portion 11.

When the apparatus 10 is inserted through the trocar incision, the tissue T as shown in FIG. 3 extends into windows 28 and 48. The cannula C limits the extent the tissue can extend into the windows. The trocar cannula C can be used in the typical fashion, i.e. providing an access port for endoscopic instrumentation to perform a laparascopic/endoscopic procedure. The apparatus 10 does not interfere with the insertion and manipulation of such instrumentation.

Figures 6, 7:
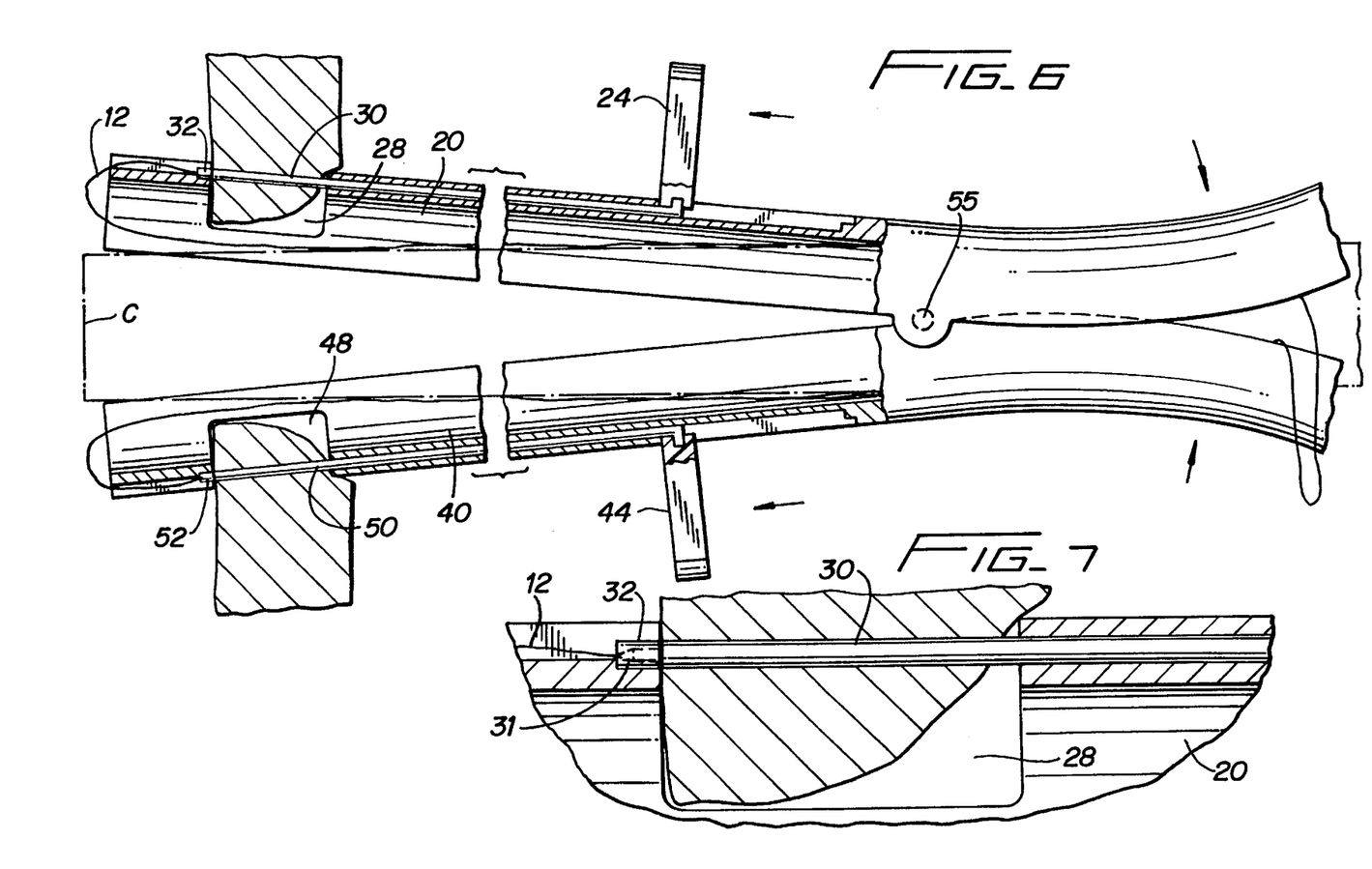
FIG. 6 is a cross-sectional view similar to FIG. 3 showing the pivoting of the elongated body halves and the advancement of the needles into engagement with the ferrules.
FIG. 7 is an enlarged cross-sectional view showing engagement of one of the needles with a ferrule.
Figure 9:
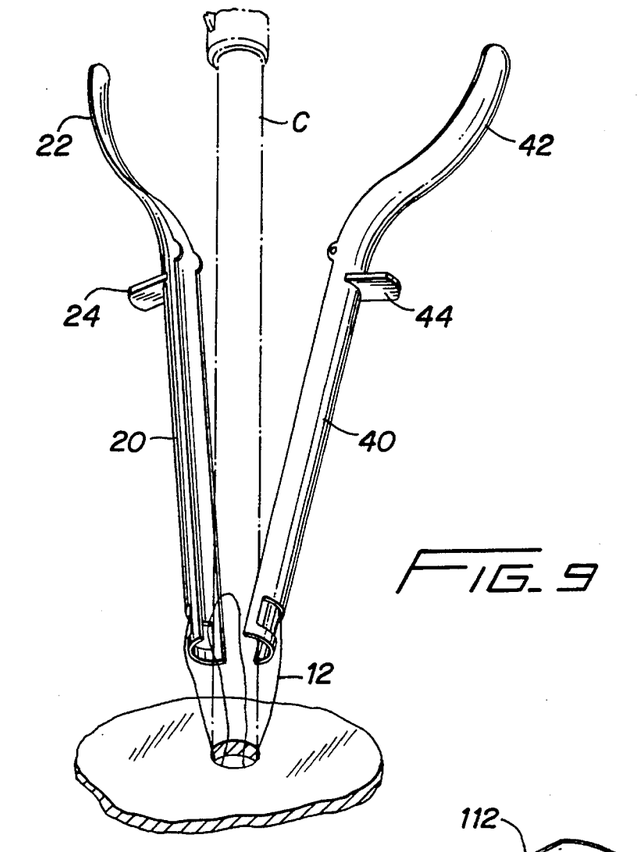
FIG. 9 is a perspective view showing the elongated body halves detached and the cannula removed from the body cavity leaving the suture in the body tissue.

At the end of the procedure, when it is desired to close the trocar incision, handles 22 and 42 are squeezed together as shown in FIG. 6, thereby pivoting the distal end portions of body halves 20, 40 away from cannula C to take a bigger bite of tissue. That is, a larger section of tissue T becomes seated in windows 28, 48 and is preferably visualized inside the body cavity by an endoscope positioned in the cavity. At this point, driver tabs 24 and 44 are slid distally to advance needles 30, 50 through the tissue positioned in windows 28, 48 and into engagement with ferrules 32, 52, respectively, to pick up suture 12 (see also FIG. 7) Driver tabs 24, 44 are subsequently slid proximally to their original retracted position, as shown in FIG. 8, thereby allowing needles 30, 50 to return to their initial rectracted positions, carrying the suture 12 through the body tissue. The two body halves 20 and 40 are then separated at pivot point 55, moved away from cannula C, and pulled further away from the body tissue along with or without the cannula as shown in FIG. 9. A loop of suture is left adjacent the innermost tissue layer, e.g. the abdominal fascia, with the suture on both sides of the wound (extending through the fascia and muscle). Suture 12 is cut at both ends to separate it from the ferrules, is tensioned to approximate the wound edges, and a knot is tied to close the incision.

Figure 10:
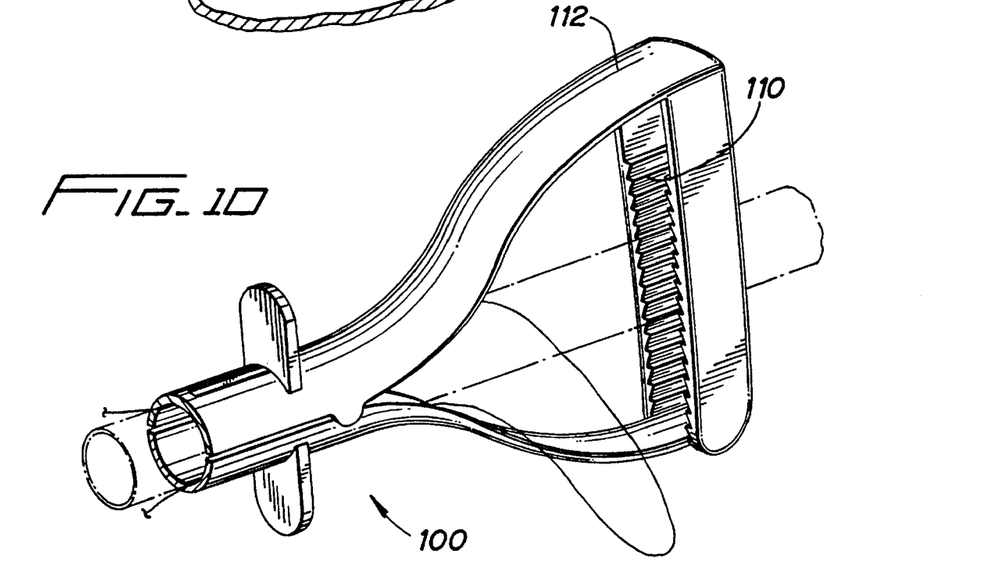
FIG. 10 is a perspective view of an alternate embodiment of the handle portion of the suturing apparatus.
Figure 11:
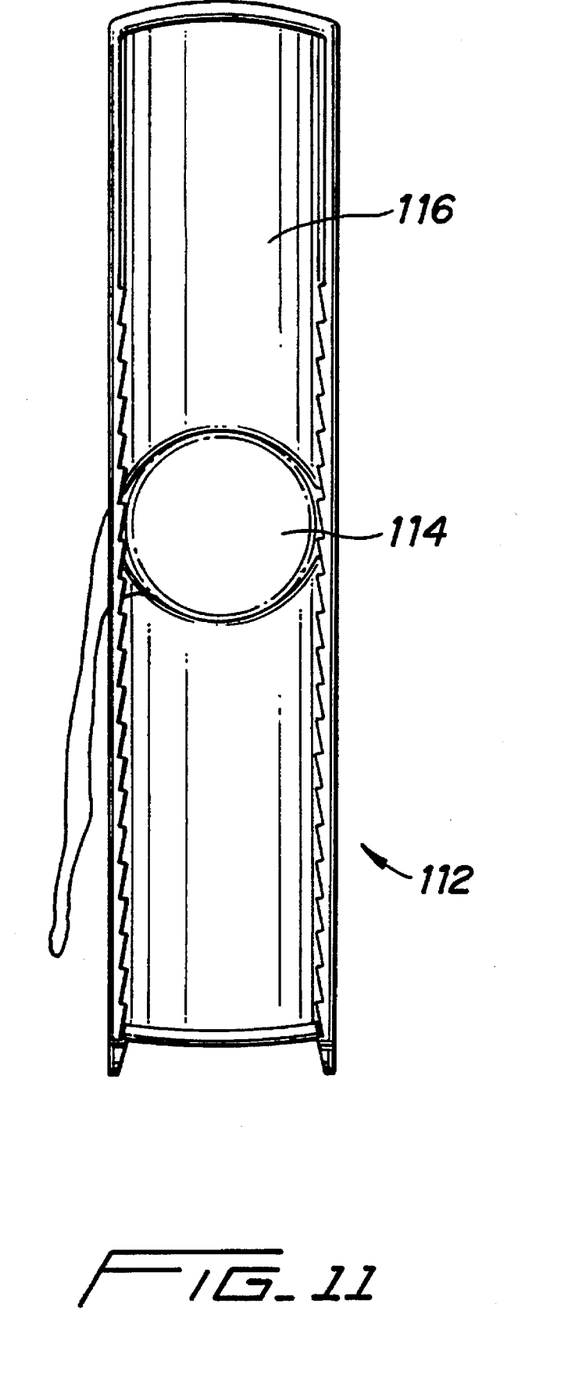
FIG. 11 is a top view of the handle of FIG. 10.

An alternate embodiment is illustrated in FIGS. 10 and 11. The apparatus 100 is identical to apparatus of FIG. 1 except for the ratchet 110 formed in handle 112 to allow for controlled and stepped spreading of the distal end portions of the body halves. Opening 114 is formed in bar portion 116 of handle 112 to accommodate the trocar cannula.

It should be appreciated, that alternatively, the apparatus 10 can be used independent of a trocar cannula. That is, the cannula can be removed prior to insertion of the apparatus 10 to close the trocar incision. Also, in some minimally invasive procedures, the instruments may be inserted directly through the body tissue to access the surgical site without the use of a cannula. The apparatus 10 can be used to close such incisions as well.

In an alternate use of the apparatus 10, the suture 12 contained in apparatus 10 is used not only to close the trocar incision but to retain a trocar cannula in position with respect to the body tissue during the surgical procedure. The suture 12 is placed in the body tissue in the manner described above, except that instead of removing the trocar cannula C, the suture is wrapped around a circumferential groove formed in the cannula or a separately mounted cannula ring fastening system such as the type described in European Patent Application No. 93115246.6, filed Sep. 22, 1993, the contents of which are incorporated herein by reference. The cannula is then used as an access port for the insertion of the desired endoscopic/laparoscopic instruments to perform the surgical procedure. At the end of the procedure, when it is desired to withdraw the cannula and close the trocar incision, the suture is unwrapped from the groove and the trocar cannula and cannula ring fastener are removed. The suture is tied to approximate the wound edges and close the trocar incision in the same manner as described above.

It should also be understood that the apparatus described herein can be used for closing other wounds and suturing other body tissue in addition to the above-described trocar incisions.

It will further be understood that various modifications may be made to the embodiments disclosed herein. Therefore, the above description should not be construed as limiting but merely as exemplifications of preferred embodiments. Those skilled in the art will envision other modifications within the scope and spirit of the claims appended hereto.

What is claimed:

1. An apparatus for suturing body tissue comprising:

first and second elongated body halves detachably connected to one another, each body half having proximal and distal portions and defining a longitudinal axis such that when the body halves are connected, the respective proximal and distal portions are positionable substantially adjacent each other;

first and second needles movable with respect to the first and second body halves, respectively, each of the needles having a penetrating tip facing in a distal direction;

at least one actuator operatively associated with the first and second needles, wherein actuation of the at least one actuator advances the first and second needles into body tissue a needle engaging member positioned in proximity to the distal portions; and a suture attached to the needle engaging member.

2. An apparatus for suturing body tissue according to claim 1, wherein the at least one actuator comprises first and second tabs slidably mounted with respect to the first and second body halves to drive the first and second needles distally into body tissue.

3. An apparatus for suturing body tissue according to claim 2, wherein each of the body halves has a window formed therein for receiving body tissue.

4. An apparatus for suturing body tissue according to claim 1, wherein the first and second body halves are detachably connected at a pivot point at the proximal end portion.

5. An apparatus for suturing body tissue comprising:

first and second elongated body halves detachably connected to one another, each body half having proximal and distal portions and defining a longitudinal axis;

first and second needles movable with respect to the first and second body halves, respectively, each of the needles having a penetrating tip facing in a distal direction;

at least one actuator operatively associated with the first and second needles, wherein actuation of the at least one actuator advances the first and second needles into body tissue;

a first ferrule positioned in the distal end portion of the first body half and a second ferrule positioned in the distal end portion of the second body half, and a suture connected at one end to the first ferrule and connected at the other end to the second ferrule, wherein actuation of the at least one actuator to advance the first and second needles advances the first needle into engagement with the first ferrule and the second needle into engagement with the second ferrule.

6. An apparatus for suturing body tissue comprising:

first and second elongated body halves detachably connected to one another, each body half having proximal and distal portions and defining a longitudinal axis;

first and second needles movable with respect to the first and second body halves, respectively, each of the needles having a penetrating tip facing in a distal direction;

at least one actuator operatively associated with the first and second needles, wherein actuation of the at least one actuator advances the first and second needles;

wherein each of the body halves has a recess for receiving body tissue, an elongated slot positioned proximally of the recess for receiving the needle, and a needle engaging member positioned distally of the recess and attached to a suture.

7. An apparatus for suturing body tissue according to claim 6, wherein upon movement of the at least one actuator, each needle is forced from the elongated slot, and into frictional engagement with the needle engaging member.

8. An apparatus for suturing body tissue according to claim 7, wherein the first and second needles are movable between a retracted position and an extended position such that upon return of the needles to the retracted position, each needle pulls the engaged needle engaging member proximally.

9. An apparatus for suturing body tissue according to claim 8, wherein each needle engaging member is substantially cylindrical in configuration and has a bore for receiving the penetrating tip of one of the needles.

10. An apparatus for suturing body tissue comprising:

an elongated body portion defining a longitudinal axis and having a proximal end portion and a distal end portion, the elongated body portion defining a central bore configured and dimensioned to permit passage of a trocar cannula through the bore, such that the cannula may extend from the distal end of the elongated body portion and being removably mountable to an outer surface of the trocar cannula, the elongated body portion further having a window to receive body tissue;

first and second needles slidably mounted within the elongated body portion to penetrate body tissue; and a suture initially spaced from the first and second needles, wherein movement of the first and second needles distally connects the first and second needles to the suture.

11. An apparatus for suturing body tissue according to claim 10, wherein the suture is connected at each end to a ferrule such that movement of the first and second needles distally moves the needles into frictional engagement with the ferrule to thereby connect the first and second needles to the suture.

12. An apparatus for suturing body tissue according to claim 11, further comprising a pair of tabs for moving the needles distally.

13. An apparatus for suturing body tissue according to claim 11, wherein the body portion comprises first and second body halves pivotably connected to each other.

14. An apparatus for suturing body tissue according to claim 13, wherein the body halves are detachably connected at a proximal end portion at a single pivot point.

15. A method for closing trocar wounds comprising:

a) providing a suturing apparatus having first and second body halves, first and second needles and a trocar cannula positioned in an axial bore thereof;

b) inserting the apparatus into the body cavity through the trocar wound;

c) advancing the first needle through the first body half and the second needle through the second body half to penetrate body tissue;

d) retracting the first and second needles within the first and second body halves, respectively; and e) separating the first and second body halves from each other.

16. A method for closing trocar wounds according to claim 15, wherein the step of advancing the first and second needles includes the step of advancing the needles in a distal direction.

17. A method for closing trocar wounds according to claim 16, wherein the step of advancing the first and second needles includes the step of connecting each needle to a portion of a suture positioned in a distal end portion of the body halves.

18. A method for closing trocar wounds according to claim 17, wherein the step of connecting each needle to a portion of the suture includes the step of each needle frictionally engaging a ferrule connected to the suture.

19. A method for closing trocar wounds according to claim 18, further comprising the steps of:

a) withdrawing the first and second body halves from the body cavity to pull the suture through the tissue;

b) removing the suture from the ferrules; and c) forming a knot in the suture outside the body cavity.

20. A method for closing trocar wounds according to claim 18, further comprising the steps of:

a) withdrawing the first and second body halves from the body cavity to pull the suture through the body tissue;

b) removing the suture from the ferrules; and c) wrapping the suture around a cannula fastening device.

* * * * *